(12) United States Patent
Miller

(10) Patent No.: US 7,575,549 B2
(45) Date of Patent: Aug. 18, 2009

(54) APPARATUS AND METHOD FOR INCREASING, MONITORING, MEASURING, AND CONTROLLING PERSPIRATORY WATER AND SOLID LOSS AT REDUCED AMBIENT PRESSURE

(76) Inventor: Sherwin Uda Miller, 85 Mt. Devon Rd., Carmel, CA (US) 93923

( * ) Notice: Subject to any disclaimer, the term of this patent is extended or adjusted under 35 U.S.C. 154(b) by 323 days.

(21) Appl. No.: 10/903,605

(22) Filed: Jul. 30, 2004

(65) Prior Publication Data
US 2005/0043595 A1 Feb. 24, 2005

Related U.S. Application Data

(60) Provisional application No. 60/497,144, filed on Aug. 22, 2003.

(51) Int. Cl.
*A61B 5/00* (2006.01)
*A61G 10/02* (2006.01)
(52) U.S. Cl. .................. 600/307; 600/300; 600/301; 128/202.12
(58) Field of Classification Search .............. 601/11; 128/202.12; 600/346, 307; 604/312
See application file for complete search history.

(56) References Cited

U.S. PATENT DOCUMENTS

| | | | | | |
|---|---|---|---|---|---|
| 2,373,333 | A | * | 4/1945 | St Onge | 165/234 |
| 4,044,772 | A | | 8/1977 | Schloss | 129/371 |
| 5,052,405 | A | * | 10/1991 | Batchelder | 600/537 |
| 5,372,126 | A | * | 12/1994 | Blau | 128/200.14 |
| 5,467,764 | A | * | 11/1995 | Gamow | 128/202.12 |
| 5,503,143 | A | * | 4/1996 | Marion et al. | 128/202.12 |
| 5,799,652 | A | * | 9/1998 | Kotliar | 128/205.11 |
| 5,850,833 | A | | 12/1998 | Kotliar | |
| 5,924,419 | A | | 7/1999 | Kotliar | |
| 5,935,516 | A | * | 8/1999 | Baugh | 422/1 |
| 5,964,222 | A | | 10/1999 | Kotliar | |
| 6,198,953 | B1 | * | 3/2001 | Webster et al. | 600/345 |
| 6,565,624 | B2 | | 5/2003 | Kutt et al. | |
| 6,595,929 | B2 | * | 7/2003 | Stivoric et al. | 600/549 |
| 6,827,760 | B2 | | 12/2004 | Kutt et al. | |
| 7,018,443 | B2 | | 3/2006 | Kutt et al. | |
| 2004/0006926 | A1 | * | 1/2004 | Neeley et al. | 52/6 |

OTHER PUBLICATIONS

"Increased Human Body Water Loss at Reduced Ambient Pressure" Sherwin U. Miller, Aerospace Medicine, vol. 33, No. 6, pp. 689-691, Jun. 1962.

* cited by examiner

*Primary Examiner*—Patricia C Mallari
(74) *Attorney, Agent, or Firm*—Patrick Reilly

(57) ABSTRACT

A device for increasing, monitoring, and measuring perspiration water and solid loss at reduced ambient pressure, comprising a sealed chamber capable of maintaining less than atmospheric pressure for an extended period of time and a gasket-sealed door accessing the chamber. The chamber provides a controlled hypobaric environment for treatment of various medical conditions. Internal controls of ambient pressure inside, temperature, humidity, oxygen, CO2 and other environmental conditions within the chamber are included, as well as a mechanism for recovering perspiration water loss from an occupant of the chamber. Methods for determining the perspiration volume of water and solid loss experienced by an occupant in the chamber are also disclosed including a computer program for determining quantity of sweat produced by the occupant of the chamber on a continuous basis. An algorithm allowing for continuous calculations of sweat loss and fluid replacement requirements of the occupant of the chamber is disclosed.

3 Claims, 4 Drawing Sheets

INPUT/OUTPUT FLOW DIAGRAM
PERSPIRATION VOLUME WATER AND SOLID LOSS
COMPUTER PROGRAM

AMBIENT AIR ENRICHED $O_2$ SYSTEM (NO MASK)

FLOW DIAGRAM OF SOFTWARE ALGORITHM FOR DETERMINATION OF SWEAT LOSS FROM BODY WEIGHT DYNAMICS $$W_1 = \Delta Wt. - W_2 - W_3 + F/EL/NR, \text{ or}$$
$$TSL = W_1$$

APPARATUS AND METHOD FOR INCREASING, MONITORING, MEASURING, AND CONTROLLING PERSPIRATORY WATER AND SOLID LOSS AT REDUCED AMBIENT PRESSURE

CROSS-REFERENCE TO RELATED APPLICATIONS

This application is related to and claims priority from Provisional Patent Application Ser. No. 60/497,144, filed Aug. 22, 2003.

BACKGROUND OF THE INVENTION

1. Field of Invention

This invention relates to apparatuses and methods for increasing, monitoring, measuring, and controlling perspiratory water and solid loss at reduced ambient pressure, for medical treatments and therapeutic applications.

2. Description of the Related Art

Normal human body temperature is maintained at a constant lever of 98.6 degrees Fahrenheit by convective, radiant, conductive, and evaporative heat loss. When the ambient pressure is reduced the heat loss through convection is reduced, and the human body compensates by increasing evaporative heat loss through the sweat glands. While an individual is at rest in this reduced pressure environment, the extent of that individual's heat loss from perspiration through millions of sweat glands will increase by several hundred percent. This heat loss due to perspiration will increase even further if that individual undergoes physical exertion, when there is an increase in the individual's metabolic rate, or when there is increased blood flow through the skin. Environmental factors can also be altered to effect perspiratory loss including ambient pressure, temperature, humidity, and the rate of air movement and quantity of air molecules in contact with the subject.

Heretofore, numerous methods and apparatuses have been developed to increase heat loss through perspiration by increasing ambient temperature in a closed vessel or chamber, Such disclosures have not, however, reduced ambient pressure or modified other environmental factors to effect this heat loss. Accordingly, a primary object of this invention is to increase the efficiency of inducing heat loss through evaporation by reducing ambient pressure and modifying other environmental factors in the chamber or vehicle where the occupant is undergoing treatment.

Prior methods and apparatuses have also been disclosed which are designed to operate at predetermined or minimally adjustable set points without any ability to control or otherwise modify the atmosphere inside the chamber or vehicle. Further these previous disclosures have been designed without any means of monitoring the vital functions of the occupants inside the chamber. Accordingly, additional objects of the invention is to provide both apparatus and means to allow precise control of the environmental factors inside the chamber and to accurately monitor and control the vital functions of the occupant(s) inside the chamber.

The loss of body-water and solid matter through sweat glands is similar, albeit substantially less efficient, to the waste removal process performed by the kidneys. When the kidneys are damaged, this waste removal process must be artificially performed through the process of renal dialysis, a time-consuming, expensive, and cumbersome procedure. It is anticipated that research testing will confirm that this invention will provide a cost effective, non-invasive method for treatment of a patient in renal failure. As such, patients in renal failure can be maintained in relative comfort for an indefinite period of time while awaiting a renal transplant, or for the return of renal function. Accordingly, another object of this invention is to provide a reasonable alternative to renal dialysis.

The present disclosures also includes a method and a unique software program and algorithm which allow for the precise determination of electrolyte loss and replacement requirements. This methodology may be used to process multiple date inputs to determine the quantity of sweat water and solid loss on a continuous basis.

The characteristics of this invention substantiate numerous other advantages and applications not anticipated by the prior art including, without limitation:

1) Providing a method for cleansing the body of the build up of toxins and impurities that contribute to the aging process;
2) Providing a method for detoxification and cleansing of circulating exogenous and endogenous toxins. Flushing the body of toxins through increase perspiration while in the chamber can effectively treat many forms of poisoning;
3) Administering hyperbaric oxygen to an occupant in the chamber;
4) Providing a method for use in the treatment of renal failure
5) Providing a method to correct fluid and electrolyte imbalances;
6) Providing a method for use in the treatment of chronic heat failure;
7) Providing a method for treating various hepatic failures;
8) Providing a method for the treatment of acute drug overdose;
9) Providing a method for the treatment of acute and chronic poisoning; and,
10) Providing a method of purging of medications when complications or side effects develop.

Additional objects and advantages of the invention will be set forth in the description which follows, and in part will be obvious from the description, or may be learned by practice of the invention. The objects and advantages of the invention may be realized and obtained by means of apparatus, methods, and combinations particularly pointed out in the appended claims.

BRIEF SUMMARY OF THE INVENTION

The present invention is an apparatus and method for increasing, monitoring, measuring, and controlling perspiratory water and solid loss at reduced ambient pressure. An apparatus is disclosed having a chamber capable of maintaining a reduced ambient pressure for a sustained period of time, and control means for controlling the environment within the chamber such as pressure, temperature, humidity, oxygen levels, CO2 levels, and the like. A methodology for determining sweat loss, solid loss, and fluid replacement requirements is disclosed including a computer program and algorithm.

BRIEF DESCRIPTION OF DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

DESCRIPTION OF THE PREFERRED EMBODIMENTS

Reference will now be made in detail to the present preferred embodiments of the invention as illustrated in the accompanying drawings.

Figure 1:
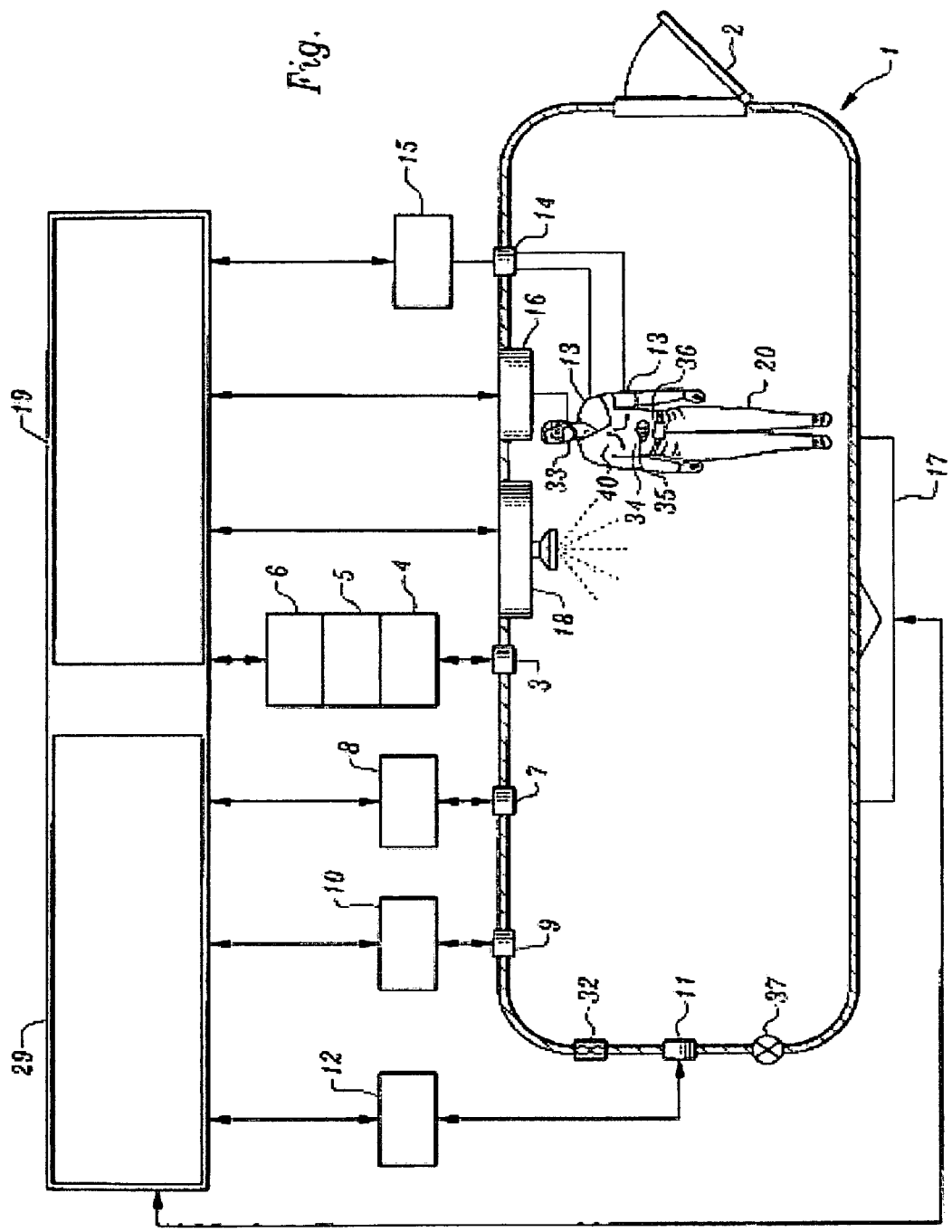
FIG. 1, schematically shows a hypobaric chamber with control means, according to the invention.
Figure 2:
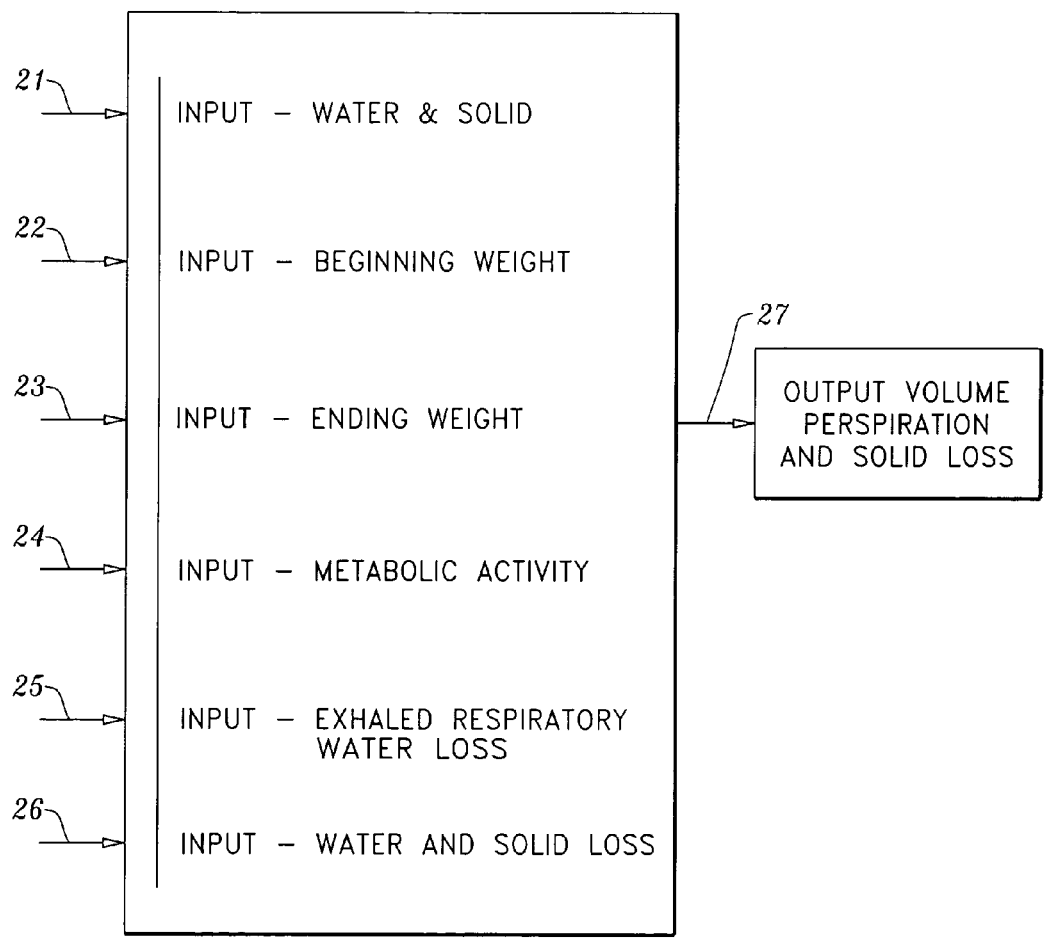
FIG. 2 shows an input/output flow diagram for a perspiration volume water and solid loss computer program, according to the invention.

In FIG. 1, a preferred embodiment of the apparatus is shown with hypobaric chamber 1, capable of maintaining a reduced ambient pressure for a sustained period of time, for the application of the present hypobaric system dialysis. Chamber 1, may be pre-fabricated so that is can be assembled from sections, and in this embodiment may include airtight ports 31, for respiratory system hoses, water and electrolyte replacement tubing, bioinstrumentation and audio video cables; its shape is variable but typically the chamber is either round or oval, but may be in other geometric configurations as well such as rectangular, square or the like. Preferably, the sections are joined by gasket-lined sides, which seal together and are maintained in position by fasteners. The rigidity and integrity of chamber 1, will not be compromised by the pressure differential between the higher external and lower internal pressures, which are typically 14.7 psi (at sea level) and 5 psi, respectively. The internal pressure can be reduced to correspond to an altitude of approximately 10,000 feet above seal level, which will further decrease convection heat loss, and correspondingly increase perspiration loss. Chamber 1, is entered through a gasket-sealed door 2, which can be opened or closed by means for a securable latch that can be opened from either side. The dimensions of chamber 1 are variable but will accommodate at least one adult male human occupant 20, comfortably and will permit that occupant 20, unrestricted freedom of movement.

It is seen in FIGS. 1-5 that the present invention provides for:
1. The hypobaric chamber, 1.
2. Access to the chamber 1 through a door with gasket seals 2.
3. An oxygen sensing device 11 and oxygen control device 12, to control the quality and supply of oxygen to the occupant 20, at the same pressure as ambient air in chamber 1.
4. An oxygen sensing device 11, and oxygen control device 12, to control the quality and supply of oxygen to the occupant 20, at the same pressure as ambient air in chamber 1.
5. A means to monitor 13, sense 14, and control 15, certain vital functions of the occupant 20, including but not limited to, sweat, blood pressure, pulse, respiration rate and depth, internal and external body temperature, and electrocardiography.
6. A CO2 removal device.
7. A means for monitoring ambient pressure 3, temperature 7, humidity 9, and other environmental factors in chamber.
8. A means for controlling the ambient pressure 4, temperature 8, and humidity 10 in chamber 1.
9. A means for providing emergency chamber re-pressurization 5.
10. A means for cleansing and sterilization of chamber 1 after use 18.
11. A means for replacing water, electrolytes, and nutritional supplements 16, for occupant 20.
12. A computer program and algorithm to process multiple data inputs to determine the quantity of sweat produced on a continuous basis.
13. A computer program for determining water volume, solid volume, and weight recovery from the inhabitant while in the chamber.
14. Methods for chamber fabrication and assembly that include factory assembly and prefabrication of the chamber with on-site assembly.

As seen in FIG. 1, the present invention can be either permanently built-in within a facility, or it can be portable. The invention may be modified so that it can be utilized in transit, or it can be transported from one location to another. Preferably, ambient air pressure is held below 7.3 psi, with the occupant 20 using a pure oxygen mask or, oxygen enriched ambient air between 7.3 and 9.3 psi is maintained.

In a preferred embodiment of the invention as seen in FIGS. 1-5, an occupant 20, enters chamber 1, through a gasket-sealed door 2. Technicians will place various bio-instrumentation monitors 13, on occupant 20 to monitor vital functions such as sweat loss, blood pressure, pulse, respiration rate and depth, internal and external body temperature, and electrocardiography. As seen in FIG. 1, bio-instrumentation monitors 13, electronically transmit information through a bio-instrumentation sensing device 14, to a bio-instrumentation control device 15, where it is processed for immediate feedback to the bio-instrumentation monitors 13, or for further transfer to control panel 19, for evaluation, recording or command signals.

Preferably, when gasket-seal door 2, closes, pressure control device 4, is activated by a signal from control panel 19. Preferably the chamber is maintained at a selected hypobaric pressures that will range from between 3.07 to 9.3 psi. A pressure transducer may be used to control operation of a vacuum pump 38, chamber air exhaust valve to maintain chamber pressure. The pressure-sensing device 3, sense any deviations or variations from the predetermined operating pressure and sends correction signals to pressure control device 4. Pressure control device 4, recycles air exhausted from chamber 1 through a filtration and sterilization device 6, which also dehumidifies the recycled air prior to reentry into chamber 1. An internal fan 32, may be used to circulate air within the chamber at a controlled rate of air movement. In the event of an emergency, chamber 1, can be immediately re-pressurized using the emergency pressurization device 5, which may be a pressure transducer operably linked to the air exhaust valve.

Preferably, ambient conditions inside chamber 1, are pre-determined and preset to maximize the efficiency of the evaporative heat loss process and minimize the amount of time occupant 20 must remain in the chamber. A temperature sensing device 7, such as a refrigeration/heater unit, sense any deviations from the preset operating temperature and sends a warning signal to temperature control device 8, which sends a correction signal. The temperature control device 8, maintains the desired operating temperature through any number of means including air-conditioning of incoming air and/or convection or radiant heating of incoming air or air inside chamber 1, Preferably temperature control device 8, is operably linked to control panel 19, and control console 29.

A humidity sensing device 9, sense any deviations from the preset operating humidity and sends a warning signal to the humidity control device, which may be a triple element drypack industrial dryer, to maintain a constant humidity. An oxygen sensing device 11, such as oxygen sensors, sense any deviation from the preset oxygen partial pressure and sends a warning signal to the oxygen control device 12, which may be a gas demand regulator, which sends a correction signal. If desired, pure oxygen may be provided to occupant 20, at the desired, preset pressure inside chamber 1. Oxygen sensing system 11, also monitors the tidal volume of oxygen exchanged and sends a warning signal to the oxygen control device 12, to either recycle or exhaust the oxygen. The system may be linked electronically to automated inlet valves 37, from oxygen supply tanks 39, and operably linked to control console 29.

Preferably, all warning and correction signals generated by the sensing and control devices are monitored at the control panel 19 on the central console 29, which have the ability to override or disable any signals generated by any other sensors. Control panel 19, preferably includes the capacity to change or alter any of the preset settings from any of the operating parameters inside chamber 1. As described in greater detail below, control panel 19, allows for monitoring occupant's water and electrolyte losses and activates the water and electrolyte replacement device 16, to administer water and electrolyte orally or intravenously.

The control panel 19, and central console 29, monitors and records the readings of the perspiration water and solid recovery device 18. The quantity of perspiration water and solid loss (or Total Sweat Loss "TSL") may be measured using a computer program, which begins the calculation by obtaining the beginning weight 22, or the occupant 20, seen in FIG. 2. The occupant's input beginning weight 22 is added to the input water and solid 21, that is, the weight of any fluids taken in through the water and electrolyte replacement device 16. The occupant's 20 input ending weight 23 is subtracted from this total to give the occupant's 20 input water and solid loss 26, which when modified to include losses from input metabolic activity 24, and input (exhaled) respiratory water loss 25, will give a quantitative value for the occupant's 20 output perspiration volume water and solid loss 27.

A sterilization and cleansing device 18, such as a spry pump, or ultraviolet lights, or the like, cleans chamber 1, by preferably spraying disinfectant over the walls and any contents inside the chamber, and sterilizing the air by means of ultraviolet lights or sterilizing chemicals.

If desired, chamber 1, may be furnished with a couch or comfortable reclining chair that is made from plastic with non-absorbent cushions, or otherwise. There may also be provided exercise equipment such as a treadmill or exercise bicycle or other ergo meter exercise equipment.

Figure 4:
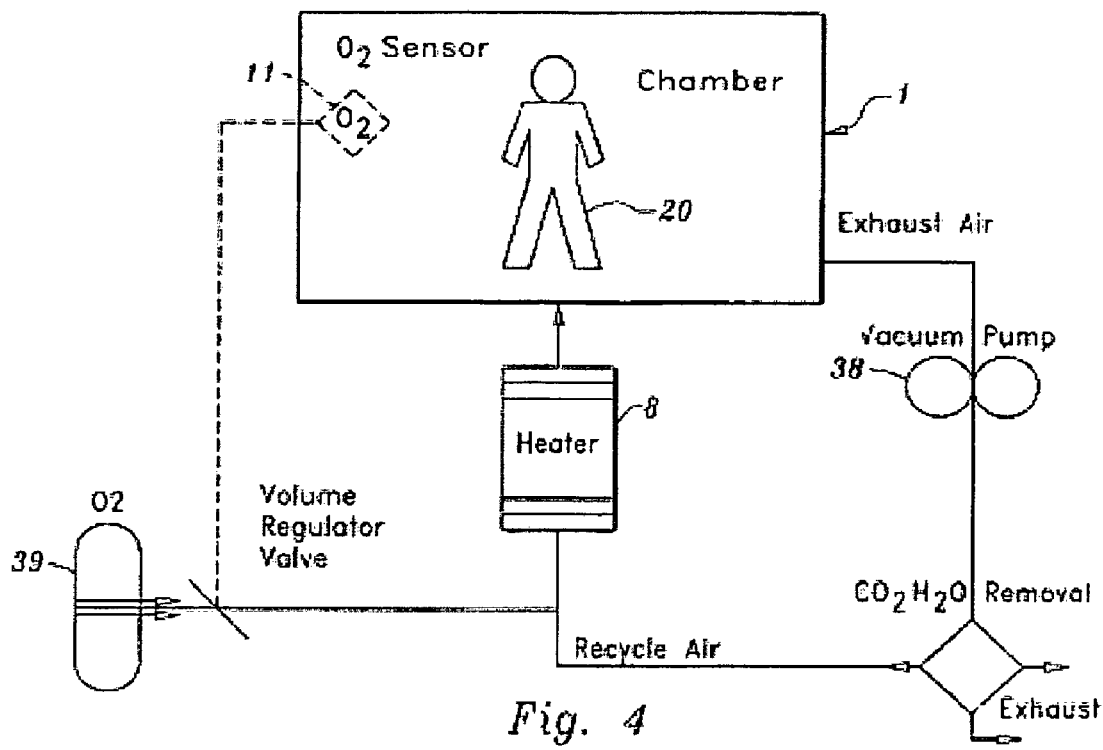
FIG. 4 shows a flow diagram of a preferred air mixture control system, according to the invention.

In a preferred embodiment, chamber testing at psi ranges from between 7.3 and 9.3 psi may be performed without a respiratory mask. The chamber ambient air may be maintained at a designated percentage level of oxygen enrichment by continuous oxygen sensors 11, which are electronically linked to automated inlet valves 37, from oxygen supply tanks and to monitoring control console 29. Preferably, carbon dioxide and water vapor are continuously monitored at the control console, and will be removed while the ambient air is recycled to maintain preset levels of carbon dioxide and humidity, as seen in FIG. 4.

Alternatively, chamber use at 3 psi to 7-psi levels will require the use of an oxygen mask. Preferably, medical grade pure oxygen is supplied to occupant 20, by an airtight bivalve mask 33, that is attached to supply tubing from an external oxygen tank. A high-pressure medical gas demand regulator maybe used to control the breathing oxygen to within 1% of internal chamber air pressure. In such use, afferent and efferent supply hoses will pass through a sealed airtight port in the chamber wall. Oxygen consumption and CO2 production are continuously monitored. The system has open and closed loop flexibility to permit expired oxygen to be either recycled or exhausted after water vapor and CO2 is removed.

In a preferred embodiment of the invention, the system provides continuous monitoring of all vital physiologic systems. The inputs from the array of monitoring equipment for the prototype test chamber are processed through unique software to provide moment-to-moment information of test results and the status of the test subjects. This information is continuously recorded and displayed at monitoring control console 29. The system will immediately detect evidence of endangering changes in the status of the test subjects while they are in the chamber.

Figure 3:
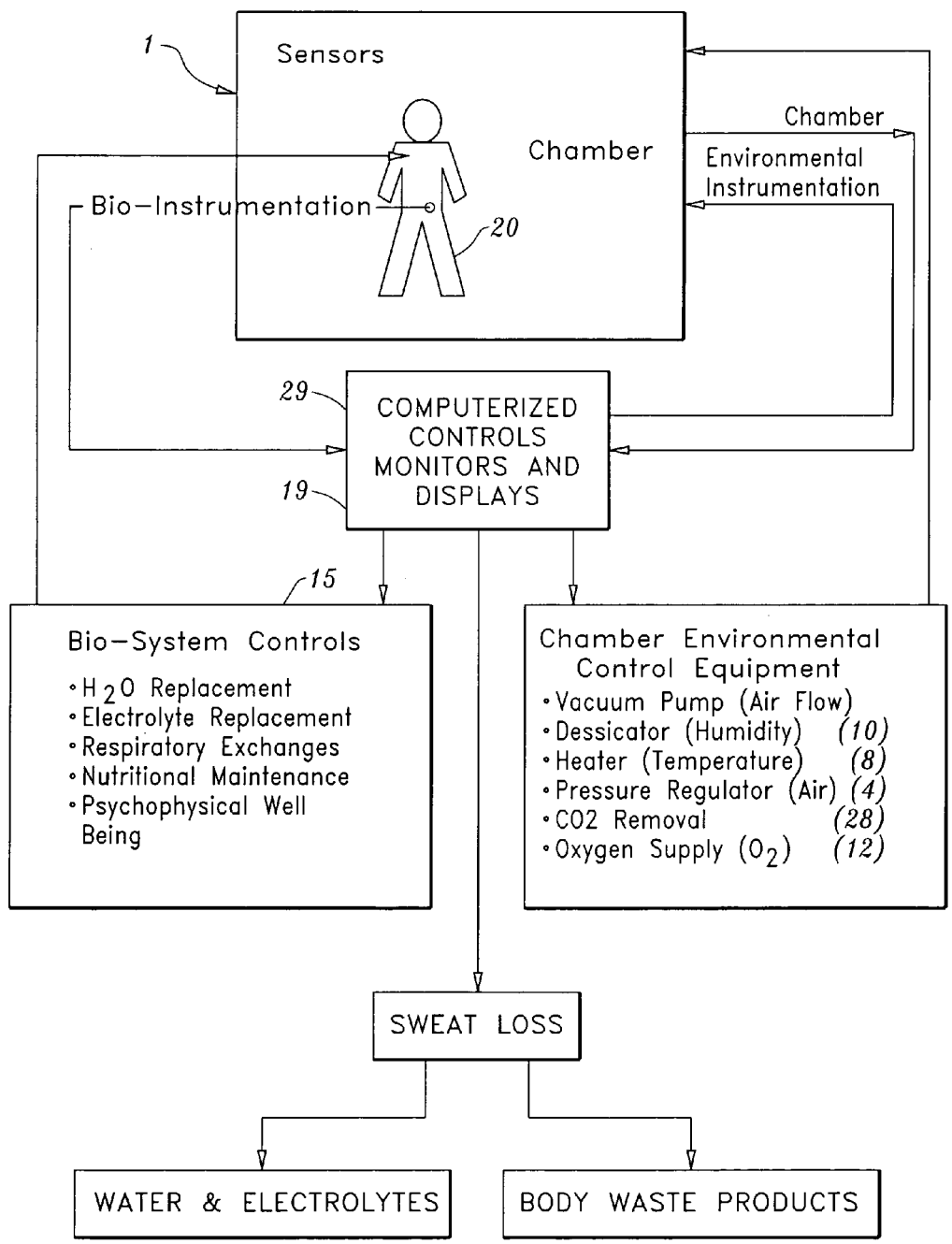
FIG. 3 is a schematic representation of a preferred control and computer system for the chamber, according to the invention.

Bioinstrumentation sensor data is linked to the environmental monitoring and control system to provide a method for automated corrective maintenance of preset ambient air composition, pressure, temperature, humidity, and airflow, as seen in FIG. 3. Precise real-time monitoring of test subject's fluid and electrolyte losses provide data that is essential to continuous fluid and electrolyte replacement. This prevents serious consequences from dehydration, hypokalemia and other electrolyte imbalances. The method used for computerized monitoring of fluid and electrolyte losses and determination of replacement requirements is described below and in FIG. 5.

The bioinstrumentation monitors, EKG; central and peripheral neurological functions; blood pressure and pulse rate using a finger plethysmograph; sweat production by GSR and epi-cutaneous water vapor analysis; respiratory rate and depth; body temperatures, including skin and core measurements; body weight dynamics; blood O2 and CO2 using transdermal sensors; overall condition and responses of test subjects (audio-video); thermal and kinetic energy production; physical activity using ergo meter exercise equipment; changes in metabolic rate; water and electrolyte replacement administered orally and/or by IV.

In a preferred embodiment, a unique software program is used to process multiple data inputs to determine the quantity of sweat produced on a continuous basis. The dynamics of sweat loss and fluid replacement requirements can be accurately determined by measuring changes in total body weight, which is continuously monitored. Sweat water and solid loss figures preferably obtained by first deducting the sum of measured losses of: (1) weight resulting from conversion of body mass into thermal and kinetic energy, plus (2) weight of pulmonary and excretory fluid and solid losses from the change in total body weight during each selected time interval while the subject is exposed to hypobaric conditions. The final step in determining sweat water and solid loss involves adding the weights of water, electrolyte, and nutritional replacement from the measured weight change during any time interval. Preferably, computations are based on the following algorithm:

$$TSL = SWV+VS-PL-KEP-TEP\ \Delta\{TBW\}=IW-SW$$
$$TSL = \Delta\{TBW\}-[TEP+KEP]-PL+EL+F/E/NR$$
$$F/E/NR \approx TSL = [PL+EL],\ or$$

In the above algorithm, the following definitions apply:
IW=Initial Weight
SW=Sequential Weight. e.g., ending weight of occupant 20 after a session in the chamber
VS=Visible Sweat
SWV=Sweat Water Vapor
$\Delta\{TBW\}$=Change in Total Body Weight resulting from a session in the chamber
TEP =Thermal Energy Production Equivalent Mass Loss KEP =Kinetic Energy Production Equivalent Mass Loss
PL=Pulmonary Water Loss. i.e. H2O weight loss through exhalation
EL=Excretory Water and Electrolyte Loss
F/E/NR=Fluid, Electrolyte, Nutritional Replacement
F/E=Fluid and Electrolyte Replacement Because of the difficulty of capturing all body sweat produced by an individual in the chamber under hypobaric conditions, the described method is preferably used to provide dynamic data on sweat production as it occurs. Measurable kinetic and thermal energy is re-converted into weight loss, and this data is factored into the continuously operating software program based on the above algorithm for calculating the volume of sweat loss as it is produced on a real-time basis. The weight of water and electrolyte replacement during an interval weight change must be treated as a factorial deduction in the above algorithm for calculating sweat loss. Preferably, replacement of water and electrolyte is synchronized with continuous computer computations of weight loss dynamics to provide moment-to-moment data on sweat production. This is shown in the algorithm flow diagram in FIG. 5.

Figure 5:
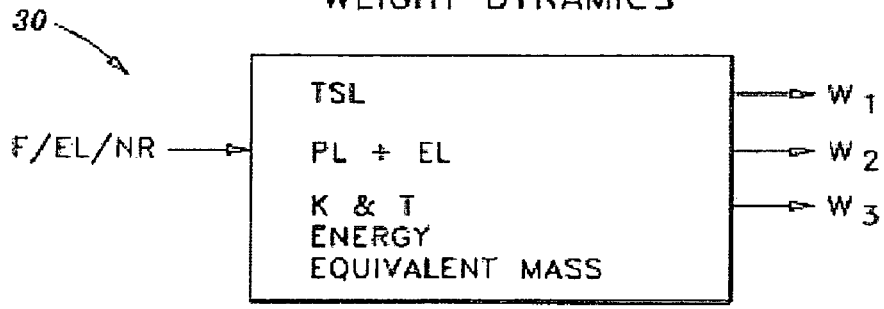
FIG. 5 shows a flow diagram of a preferred software algorithm for determination of sweat loss from body weight dynamics, according to the invention.

In the algorithm flow diagram seen in FIG. 5, the change in body weight ($\Delta$Wt.) during any interval period is the sum of the weights of sweat loss (W1) plus pulmonary (PL) and excretory (EL) water and solid loss (W2) plus the equivalent mass losses from kinetic (KEP) and thermal (TEP) energy production (W3). The weights of energy equivalent weight loss are deducted from the total interval weight loss to determine total sweat loss TSL. The weight of fluid, electrolyte and nutritional replacement (F/E/NR) is added to the interval weight change to determine sweat loss during the interval period.

Sweat remaining on the skin results in decreased sweating (hypohidrosis) so it is essential to use a method for the continuous removal of sweat that accumulates on the skin. Increasing the airflow over the skin tens to negate the sweat stimulating effect of reduced convective heat loss resulting from lowering ambient pressure. When the rate of air molecular contact with the skin increases as a result of rapid airflow, the increase in convective evaporative heat loss will tend to match the convective loss at a higher ambient pressure. Accordingly, the present method preferably uses a thermal regulated garment 34, having an internally porous material that removes sweat by vacuum as it forms on the skin. The garment, schematically represented in FIG. 1, may include a inner layer mesh of small perforated flexible plastic tubes 35, that surround the body and that are connected to a vacuum pump 36, that continuously removes sweat as it forms on the skin. The outer layer 40, of garment 34, is a thermal blanket which can be either electrically or radiantly heated or cooled with thermally regulated fluid supplied by a source outside of chamber 1.

As is evident from the above description, a wide variety of applications, methods, and systems may be envisioned from the disclosure provided. The apparatus and methods described herein are applicable in various types of renal failure ranging from acute uremia to ESRD; fluid and electrolyte disturbances; chronic heart failure; hepatic failure; acute and chronic poisoning; acute drug overdose; and purging of medications, such as aiding in the rescue of cancer patients showing evidence of hepatic-renal failure an/or hematological complications of chemotherapy), and additional advantages and modifications will readily occur to those skilled in the art. The invention in its broader aspects is, therefore, not limited to the specific details, representative apparatus and illustrative examples shown and described. Accordingly, departures from such details may be made without departing from the spirit or scope of the applicant's general inventive concept.

What is claimed is:

1. A method for determining the perspiration volume of water and solid loss experienced by an occupant in a sealed chamber, comprising the steps of:
   monitoring the water and solid input;
   calculating an input weight gain by the occupant derivable from the monitoring data of the water and solid input;
   receiving a measurement of the beginning weight of said occupant in said chamber;
   receiving a measurement of the ending weight of said occupant of said chamber;
   monitoring the metabolic activity experienced by said occupant of said chamber;
   calculating a metabolic weight loss derivable from the monitored occupant's metabolic activity experienced by said occupant of said chamber; and
   using a computer program embodied on a computer readable medium, calculating the perspiration volume water and solid loss.

2. The method of claim 1, wherein said method further includes using a computer program means for determining quantity of sweat produced by said occupant of said chamber on a continuous basis.

3. The method of claim 2, wherein said computer program utilizes an algorithm allowing for continuous calculations of sweat loss and fluid replacement requirements of said occupant of said chamber.

* * * * *